(12) United States Patent
Moskovich

(10) Patent No.: US 8,281,446 B2
(45) Date of Patent: Oct. 9, 2012

(54) ORAL CARE IMPLEMENT

(75) Inventor: Robert Moskovich, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 42 days.

(21) Appl. No.: 12/564,463

(22) Filed: Sep. 22, 2009

(65) Prior Publication Data

US 2010/0010523 A1    Jan. 14, 2010

Related U.S. Application Data

(60) Division of application No. 10/989,267, filed on Nov. 17, 2004, now Pat. No. 7,607,189, and a continuation-in-part of application No. 29/209,242, filed on Jul. 14, 2004, now abandoned, and a continuation-in-part of application No. 29/209,244, filed on Jul. 14, 2004, now abandoned.

(51) Int. Cl.
*A61B 17/24* (2006.01)
*A61H 13/00* (2006.01)

(52) U.S. Cl. ............... 15/111; 15/110; 15/187; 15/188; 601/141; 606/161

(58) Field of Classification Search .................. 15/110, 15/111, 187, 188; 601/137–139, 141; 606/161
See application file for complete search history.

(56) References Cited

U.S. PATENT DOCUMENTS

| | | | |
|---|---|---|---|
| 697,336 A | 4/1902 | Hagerty | |
| 1,002,468 A | 9/1911 | Strangman | |
| 1,125,532 A | 1/1915 | Himmel | |
| 1,128,139 A | 2/1915 | Hoffman | |
| 1,405,279 A | 1/1922 | Cassedy | |
| 1,817,585 A | 8/1931 | Samuel | |
| 1,872,832 A | 8/1932 | Silverberg | |
| 1,892,068 A | 12/1932 | Metzler | |
| 1,903,161 A | 3/1933 | Barkan | |
| 1,993,662 A | 3/1935 | Green | |
| D99,352 S | 4/1936 | Grapp | |
| 2,049,956 A | 8/1936 | Greenberg | |
| 2,218,072 A | 10/1940 | Runnels | |
| 2,233,936 A | 3/1941 | Campbell | |
| 2,253,210 A | 8/1941 | Psiharis | |
| 2,253,910 A | 8/1941 | Luenz | |
| 2,418,485 A | 4/1947 | Shipley | |
| 2,512,059 A | 6/1950 | Haeusser | |
| 2,543,999 A | 3/1951 | Voss | |
| 2,583,750 A | 1/1952 | Runnels | |
| 2,642,604 A | 6/1953 | Ferrari | |
| 4,827,551 A | 5/1989 | Maser et al. | |
| 5,027,796 A | 7/1991 | Linzey | |
| 5,613,262 A | 3/1997 | Choy-Maldonado | |
| 5,765,252 A | 6/1998 | Carr | |
| 5,779,654 A | 7/1998 | Foley et al. | |

(Continued)

FOREIGN PATENT DOCUMENTS

DE    857 128 C    11/1952

(Continued)

*Primary Examiner* — Mark Spisich
(74) *Attorney, Agent, or Firm* — Amy M. Fernandez

(57) ABSTRACT

An oral care implement including a handle and a head with a tongue cleanser. The tongue cleanser has at least one ridge which is at least as wide as it is high. In one preferred construction, the ridges are shaped so as to define a concave surface facing generally toward the handle. The ridges also preferably include aligned segments from front to back that are oriented at different angular positions.

3 Claims, 11 Drawing Sheets

U.S. PATENT DOCUMENTS

| | | | |
|---|---|---|---|
| D397,219 S | 8/1998 | Rangel et al. |
| 5,792,159 A | 8/1998 | Amin |
| 5,810,856 A | 9/1998 | Tveras |
| 5,967,152 A | 10/1999 | Rimkus |
| 5,980,542 A | 11/1999 | Saldivar |
| 5,984,935 A | 11/1999 | Welt et al. |
| 6,004,334 A | 12/1999 | Mythen |
| 6,015,293 A | 1/2000 | Rimkus |
| 6,032,315 A | 3/2000 | Liebel |
| 6,119,296 A | 9/2000 | Noe et al. |
| 6,131,228 A | 10/2000 | Chen et al. |
| 6,254,390 B1 | 7/2001 | Wagner |
| D447,238 S | 8/2001 | Tang |
| 6,273,719 B1 | 8/2001 | Whitman |
| 6,319,332 B1 | 11/2001 | Gavney, Jr. et al. |
| 6,352,545 B1 | 3/2002 | Wagner |
| RE37,625 E | 4/2002 | Wieder et al. |
| D461,959 S | 8/2002 | Chan et al. |
| 6,440,149 B1 | 8/2002 | Potti |
| 6,463,619 B2 | 10/2002 | Gavney, Jr. |
| D465,847 S | 11/2002 | Jacobs |
| D471,276 S | 3/2003 | Potti |
| 6,571,417 B1 | 6/2003 | Gavney, Jr. et al. |
| 6,792,642 B2 | 9/2004 | Wagstaff |
| 6,820,299 B2 | 11/2004 | Gavney, Jr. |
| 6,865,767 B1 | 3/2005 | Gavney, Jr. |
| 2003/0115699 A1 | 6/2003 | Wagstaff |
| 2003/0216762 A1 | 11/2003 | Levit |
| 2004/0031115 A1 | 2/2004 | Gavney, Jr. |
| 2004/0134007 A1 | 7/2004 | Davies |
| 2004/0200748 A1 | 10/2004 | Klassen et al. |
| 2000/4023107 | 11/2004 | Gavney, Jr. |
| 2004/0221409 A1 | 11/2004 | Gavney, Jr. |
| 2004/0237236 A1 | 12/2004 | Gavney, Jr. |
| 2004/0255416 A1 | 12/2004 | Hohlbein |
| 2005/0000049 A1 | 1/2005 | Hohlbein |
| 2005/0015904 A1 | 1/2005 | Gavney |
| 2005/0038461 A1 | 2/2005 | Phillips |

FOREIGN PATENT DOCUMENTS

| | | |
|---|---|---|
| DE | 201 07 614 U1 | 9/2002 |
| DE | 101 22 987 A1 | 11/2002 |
| DE | 20 2005 009 026 U1 | 10/2005 |
| EP | 1 034 721 A | 9/2000 |
| JP | 308522 | 11/2000 |
| JP | 142867 | 5/2002 |
| WO | 9808458 A | 3/1998 |
| WO | 0145573 | 6/2001 |
| WO | 02062174 | 8/2002 |
| WO | 0117433 A | 3/2003 |

ORAL CARE IMPLEMENT

RELATED APPLICATIONS

This application is a continuation-in-part application of U.S. patent application Ser. No. 29/209,242, filed Jul. 14, 2004, abandoned, and a continuation-in-part application of U.S. patent application Ser. No. 29/209,244, filed Jul. 14, 2004, abandoned, and a divisional of U.S. patent application Ser. No. 10/989,267 filed Nov. 17, 2004, now U.S. Pat. No. 7,607,189, the contents of which are incorporated herein by reference in their entirety for all purposes.

FIELD OF THE INVENTION

The present invention pertains to an oral care implement with a cleanser for the tongue and other soft tissue in the mouth, such as the inner surfaces of the cheeks.

BACKGROUND OF THE INVENTION

According to the American Dental Association, a major source of bad breath in healthy people is microbial deposits on the tongue. Due to its papillary nature, the tongue creates a unique ecological site that provides a large surface area, favoring the accumulation of oral bacteria. Anaerobic flora and bacteria residing on the tongue can lead to the development of chronic bad breath commonly called halitosis. In general, the bacteria produce volatile sulfur compounds (VSC). If there is enough buildup of the sulfur compounds, bad breath or oral malodor may result.

While tongue scrapers have been used in the past, these scrapers have not adequately met the need. Past scrapers have typically been taller than they are wide thus risking injury to the user, insufficiently supported, and/or lacking beneficial shapes. Hence, there is a need for an oral care implement with a tongue cleanser that provides effective removal of bacteria and other debris.

BRIEF SUMMARY OF THE INVENTION

The invention pertains to an oral care implement with a tongue cleanser that provides improved cleaning and effective removal of bacteria and micro debris disposed on the tongue as well as other oral tissue surfaces.

In one aspect of the invention, the tongue cleanser includes at least one ridge that includes a contact region for engaging and cleaning the tongue or other soft tissue in the mouth. The contact region defines a width transverse to the length of the ridge that is at least as large as the height of the ridge from the head. In this way, there is a reduced risk that users may injure themselves.

In one other aspect of the invention, the tongue cleanser includes at least one ridge to engage and cleanse the tongue. Each ridge is at least as wide at its base as it is tall to provide sufficient support for the ridge to be dragged across surfaces within the mouth. With this construction, the ridges are generally maintained in a protruding manner to effectively clean the tongue of bacteria and debris.

In another aspect of the invention, the tongue cleanser includes a plurality of spaced apart ridges shaped to present a concave side facing the handle of the oral care implement. The ridges are also preferably formed with a successively broader curve as the ridges are positioned farther from the handle.

In another aspect of the invention, the tongue cleanser includes a plurality of ridge segments that are aligned from front to back at different angular orientations. This construction enables successive ridges to engage the tongue at different angular orientations as the tongue cleanser is moved across the tongue for effective cleaning of the tongue surface.

In another aspect of the invention, an oral care implement is provided with tooth cleaning elements and a tongue cleanser for a thorough cleaning of the mouth. In a preferred construction, the tooth cleaning elements and tissue cleanser are supported on opposite sides of a head.

DETAILED DESCRIPTION OF THE INVENTION

Figure 1:
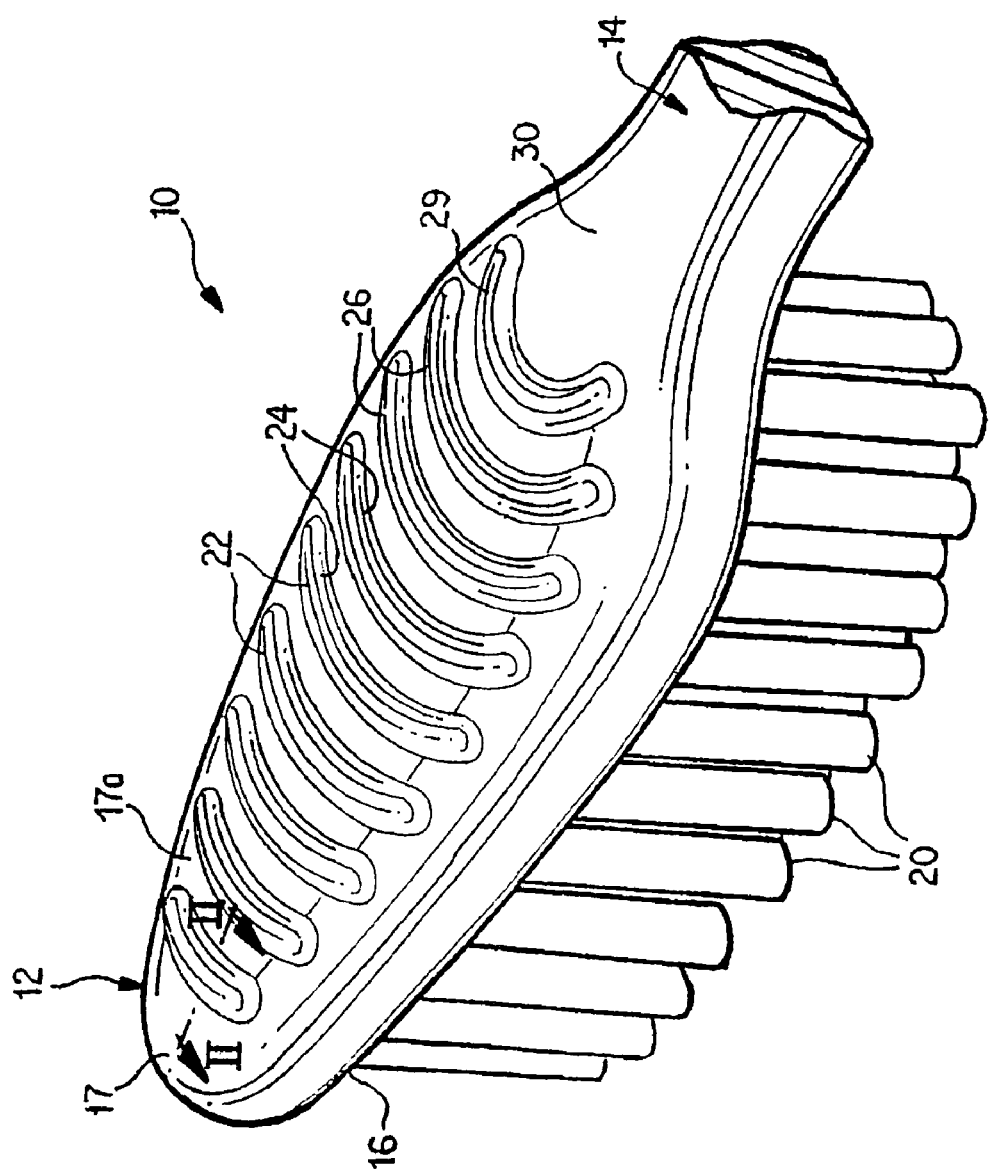
FIG. 1 is a perspective view of a head of a toothbrush in accordance with the present invention.

In the following description, the invention is discussed in terms of a toothbrush, but could be in the form of other oral care implements including simply a tissue cleansing implement. Further, it is to be understood that other embodiments may be utilized and structural and functional modifications may be made without departing from the scope of the present invention.

An oral care implement in accordance with the present invention is illustrated in the form of a toothbrush 10 including a head 12 and a handle 14. While FIG. 1 only illustrates the connection of the handle to the head, the handle is preferably an elongate member to be grasped by the user. The handle 14 could have any known shape adapted for the manipulation needed to clean the teeth and/or tongue of a user.

The head 12 with a pair of opposite sides 16, 17 is shown with a generally oblong shape, although other known shapes could be used. A plurality of teeth cleaning elements 20 extend from one side 16 of the head 12. The teeth cleaning elements could be bristles and/or elastomeric members of various shapes and sizes. Any form or combination of elements 20 suitable for cleaning a user's teeth could be used.

The other side 17 of head 12 includes at least one ridge and preferably a plurality of elongate ridges 22 to cleanse the tongue and other soft tissue of the mouth (e.g., the inner surfaces of the cheeks). While the ridges are preferably formed on a head also provided with teeth cleaning elements, they could also be formed on other implements or other parts of the toothbrush. A head of the implement is simply meant to be the operative portion of the implement that is inserted into the mouth for cleaning of the tongue, and does not refer to a particular shape or structure of the head.

Figure 2:
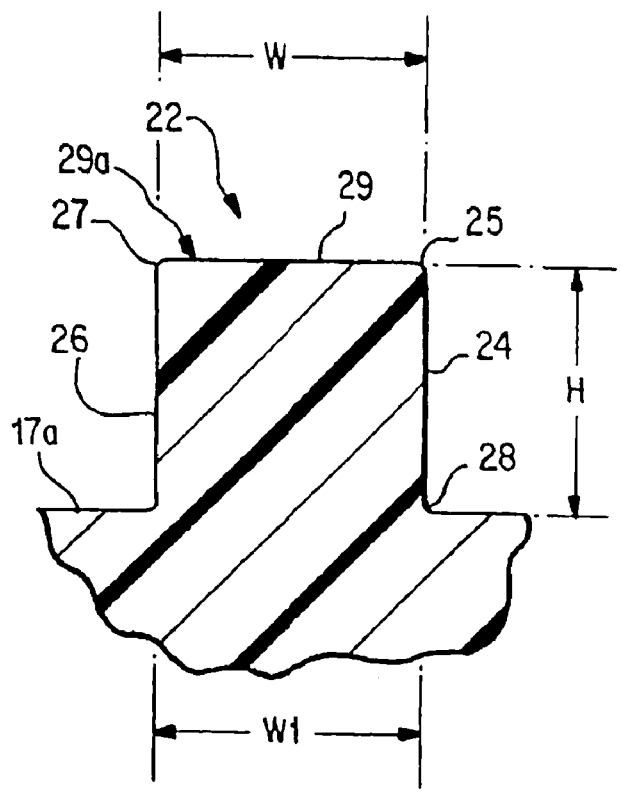
FIG. 2 is a partial cross-sectional view taken along line II-II in FIG. 1.

In one constriction of the invention, each ridge 22 projects orthogonally from a back surface 17a of the head and has a generally square-like cross-sectional configuration (FIG. 2). The ridge includes a distal end 29 remote from surface 17a that forms a contact region 29a adapted to contact and clean the tongue or other soft tissue in the mouth. In this embodiment, the contact region 29a is defined between and includes protruding corners or edges 25, 27. As can be appreciated, the contact region 29a has a width W extending transverse to the extension of the ridge across surface 17a. The width W of ridge 22 is at least as large as the height H of the ridge (i.e., the distance the ridge extends from surface 17a). With this width to height relationship, the risk of the ridge cutting or injuring the soft tissue of the tongue or other parts of the mouth is reduced. A narrow ridge that extends outward from head 12 a distance greater than its width has an increased risk of cutting or otherwise injuring the user as compared to a similarly narrow ridge (i.e., one with the same width) that extends from the head a distance less than the width of the ridge; such a ridge will not tend to cut or hurt the user. The tongue and other soft tissue in the mouth will give and bend some distance around the ridge so long as the ridge is not too tall for the width of the ridge engaging the tissue. In one exemplary embodiment, ridges 22 have a width W that is preferably about 0.8 mm and a height H about 0.6 mm. Nevertheless, a wide range of relative sizes are possible.

Additionally, ridge 22 also includes a base 28 where the ridge is fixed to surface 17a. In a preferred construction, base 28 defines a width W1 that is at least as large as the height H of the ridge. In this way, the ridges do not experience undue bending as they are dragged over the tongue. Rather, ridges 22 are stably supported so that they tend to remain generally in a protruding orientation. As a result, edges 25, 27 are stably supported to dig into recesses in the tongue to effectively remove bacteria and debris.

Figure 3:
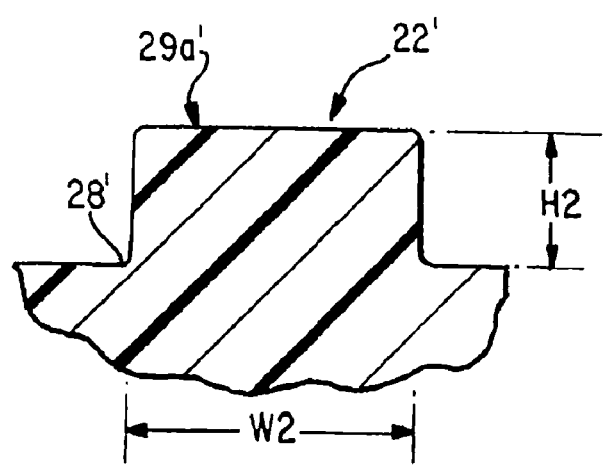
FIG. 3 is a partial cross sectional plan view of an alternative structure taken along line II-II of FIG. 1.

Alternatively, the ridges could have other shapes. For example, FIG. 3 illustrates ridges 22' that are substantially wider than they are tall, i.e., base 28' and contact region 29a' each has a width W2 that is substantially greater than the height H2 of the ridge. In one example, the width is about twice the distance of the height. The increased width to height ratio of ridge 22' provides for a stiffer, smaller ridge to effectively cleanse the tongue. Such ridges are beneficial in that they reduce the size of the head, which is preferred by some users. A shorter, wider ridge also further reduces the prospect of users injuring themselves. Moreover, such ridges can be made of softer materials without losing the desired stability.

Figure 3A:
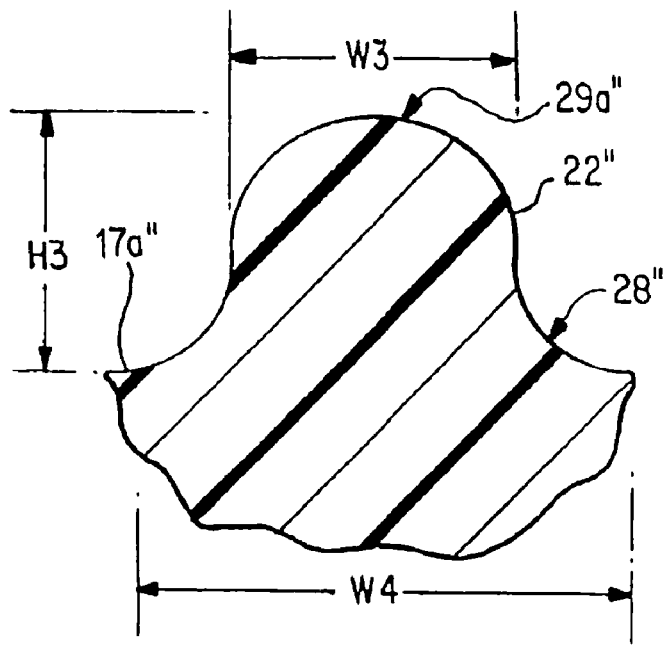
FIGS. 3a and 3b are partial cross-sectional views of alternative ridge shapes.

In another example (FIG. 3a) ridge 22" has a rounded distal end. Accordingly, the contact region 29a" has an arcuate, convex surface to engage the tongue or other soft tissue. In this example, the contact region 29a" (i.e., the surface adapted to engage the tongue) has a width W3 that is at least as large as the height H3 of the ridge. In this embodiment, the base 28" of ridge 22" also has a width W4 that is at least as large as height H to present a stable ridge. Of course, numerous variations may be formed in the shape of the ridge while maintaining the benefits of the invention.

Figure 3B:
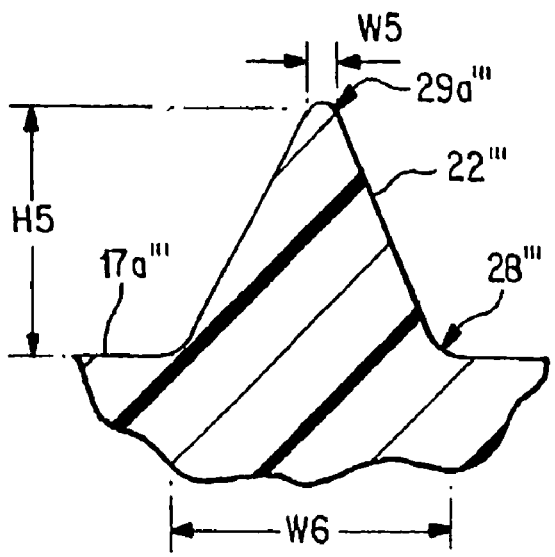

In addition, the ridges may be formed to gain only some of the benefits of the invention. For instance, ridge 22''' can be formed to taper to a narrowed distal end 29''' (FIG. 3b). In this instance, contact region 29a''' has a width W5 that is less than the height H5. However, the base 28''' of ridge 22''' has a width W6 that is at least as large as the height to form a stable ridge construction.

Although the illustrated ridges have all been shown to extend generally perpendicular from surface 17a, they could be inclined relative to surface 17a. A perpendicular extension is preferred to provide effective cleaning regardless of whether the tongue cleaner is pushed or pulled over the tongue. The sides 24, 26 could also be inclined, curved, angular, irregular or otherwise shaped. Additionally, the ridges could project from a non-planar surface. As one example, surface 17a and ridges 22 could have an undulating configuration.

Regardless of the cross-sectional shape of the ridge, each ridge 22 is preferably curved to define a concave side 24 facing toward handle 14 and a convex side 26 facing in the opposite direction. Although ridges that are continuously curved are preferred (FIG. 1a), such concave-shaped ridges could be defined by non-continuous ridges (FIG. 1b) or angular ridges (FIG. 1c). Further, in one preferred construction, ridges 22 are progressively less curved as they are formed farther from handle 14. In one illustrated construction (FIGS. 1 and 1a), the ridges are generally concentric to each other curving generally about a common point near the connection of handle 14 to head 12.

In use, the user grips the handle and typically pulls the tongue cleanser repeatedly over the tongue from back to front so that the concave sides 24 are scraped against the tongue to effectively gather and remove bacteria and debris on the tongue. Alternatively, the user may also commonly move the tongue cleanser forward and backward over the tongue. In either event, the different curvatures of the ridges enable aligned segments of the ridges (i.e., along lines generally parallel to longitudinal axis 30) to engage the tongue surface at different angles for effective cleaning of the tongue. Nevertheless, the tongue cleansing ridges can be moved over the tongue in a number of ways to clean the tongue.

Figure 4:
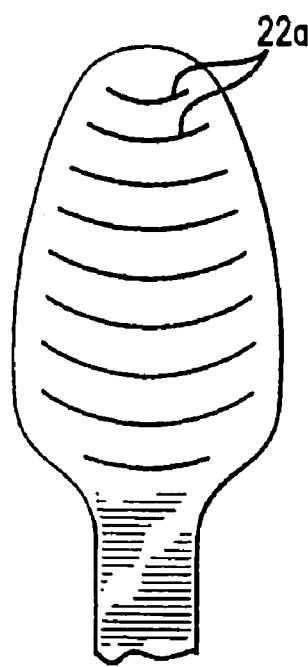
FIGS. 4-17 are each a top plan view of the head illustrating an alternative ridge construction.
Figure 5:
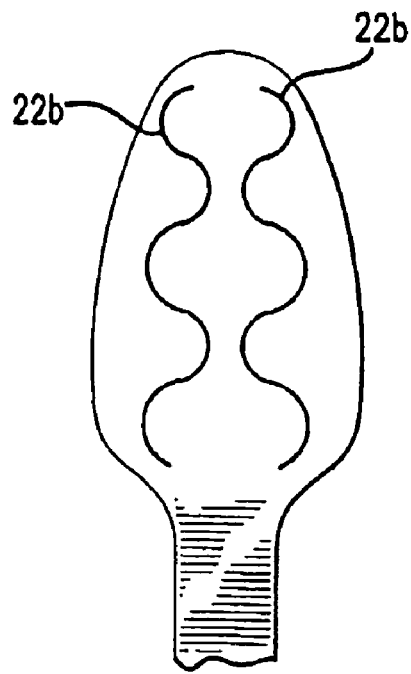
Figure 6:
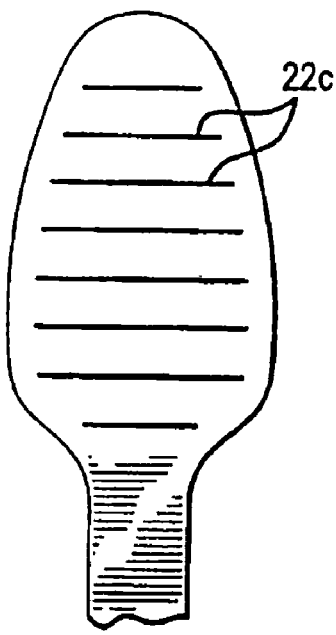
Figure 7:
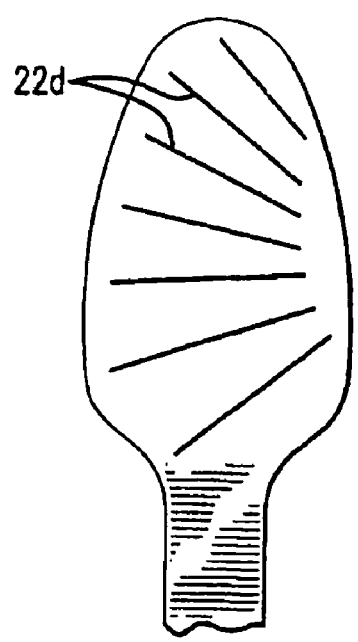
Figure 8:
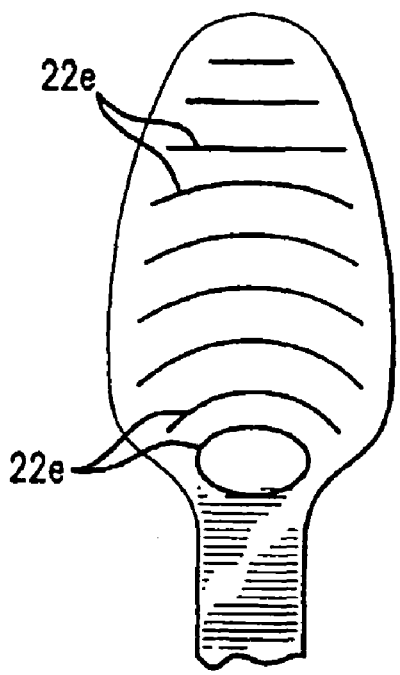
Figure 9:
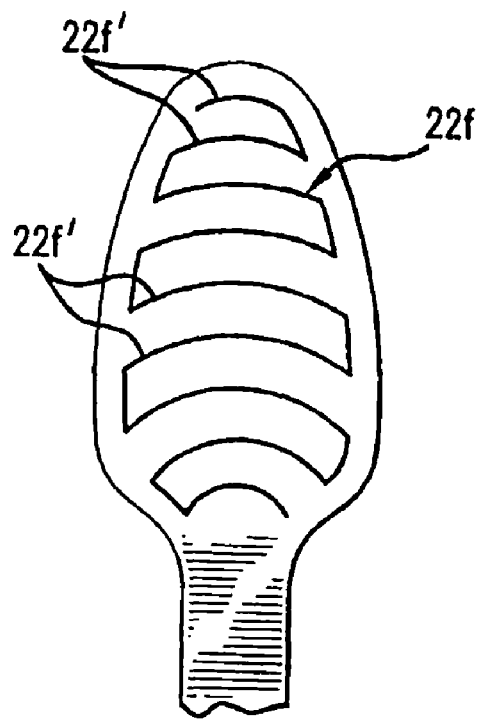
Figure 10:
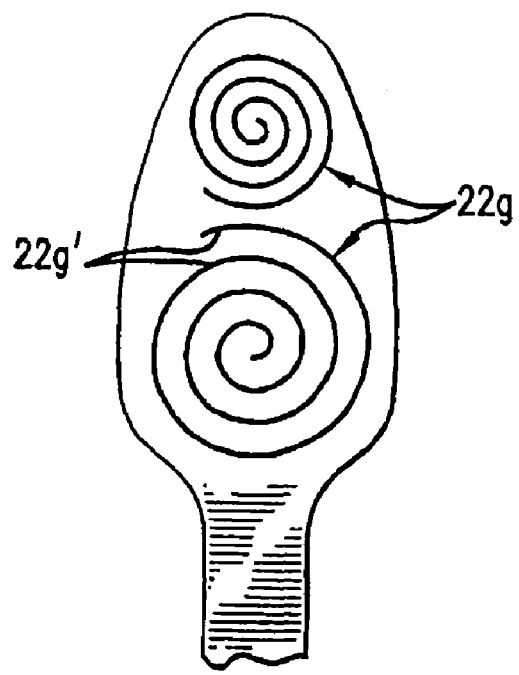
Figure 11:
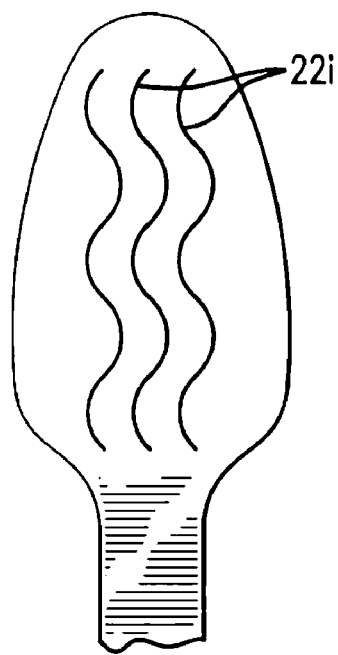
Figure 12:
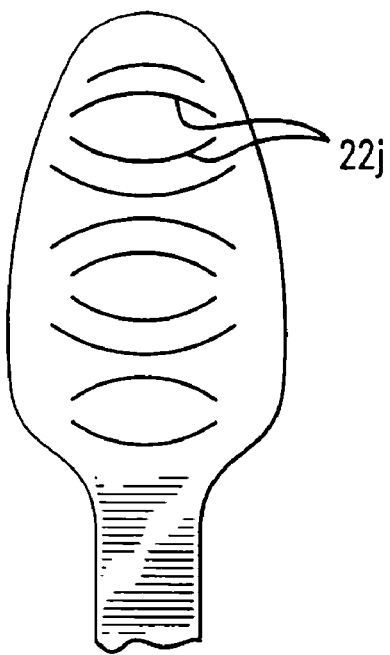
Figure 13:
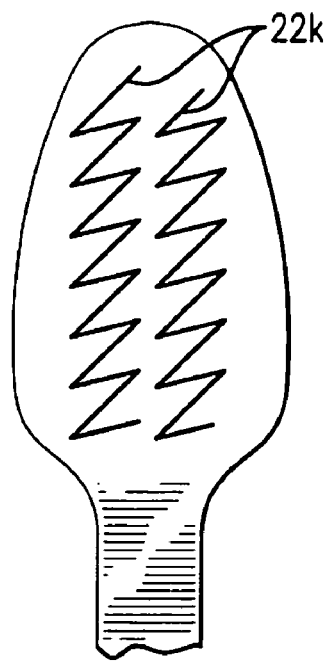
Figure 14:
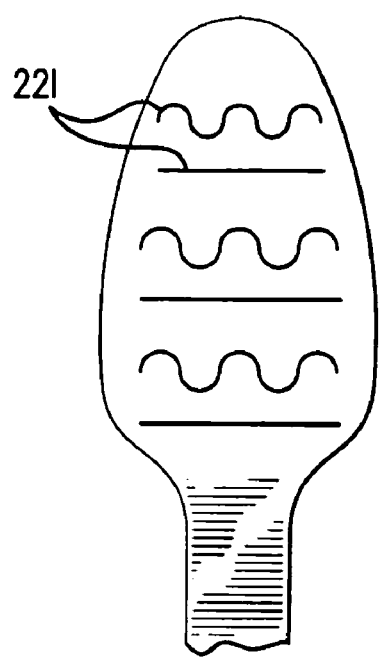
Figure 15:
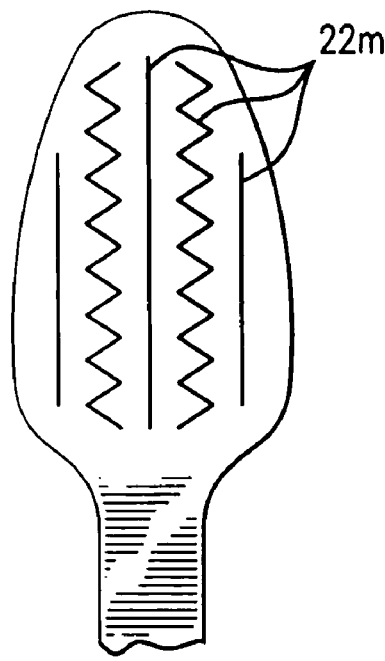
Figure 16:
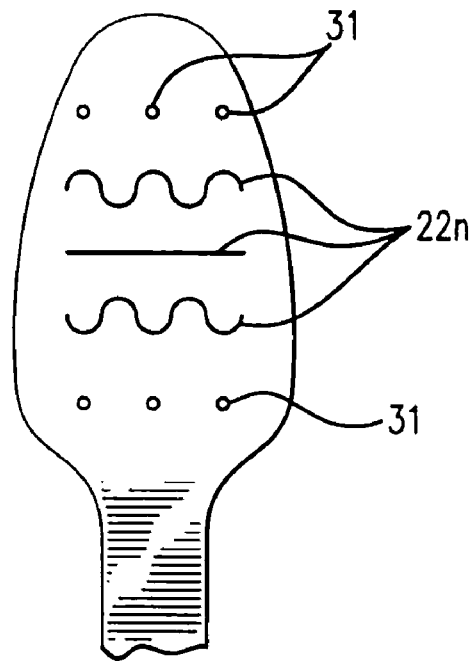
Figure 17:
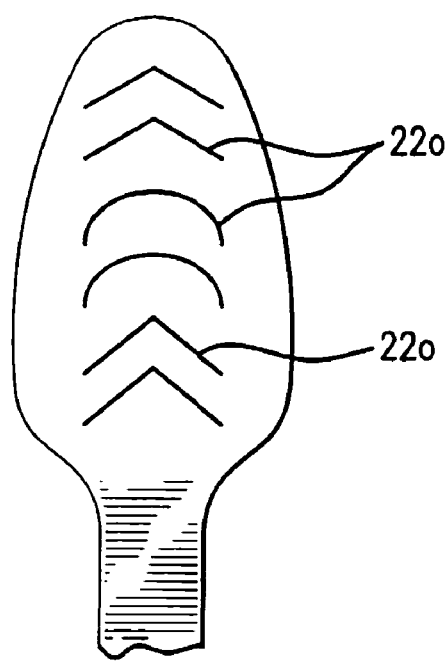
Figure 18:
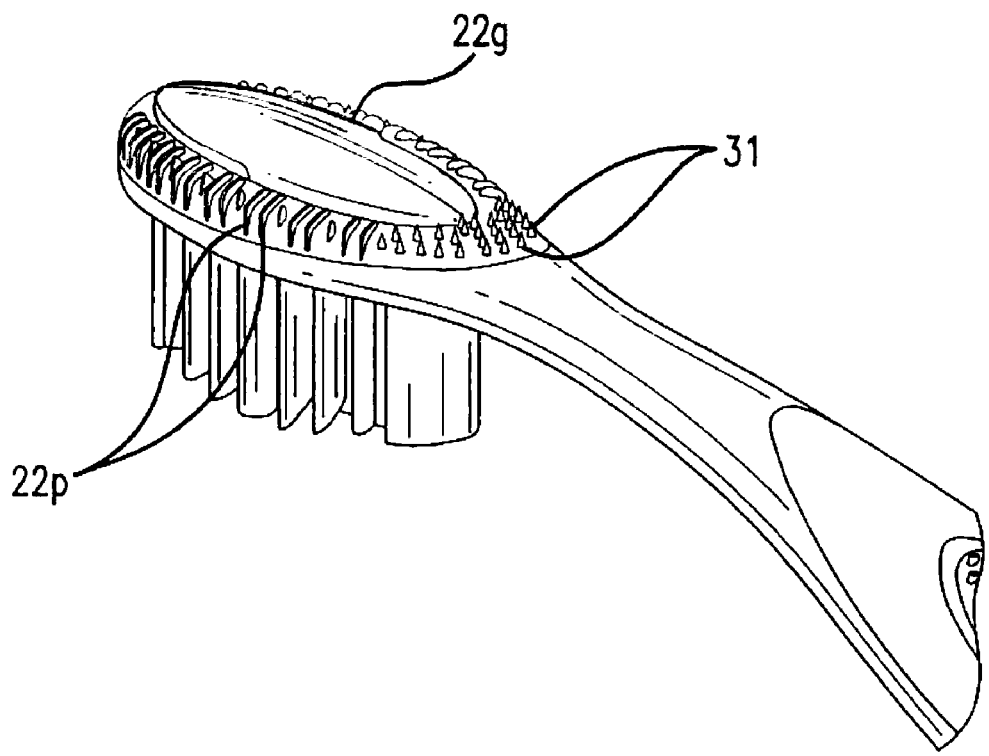
FIGS. 18-22 are each a perspective view of a head with an alternative ridge construction.
Figure 19:
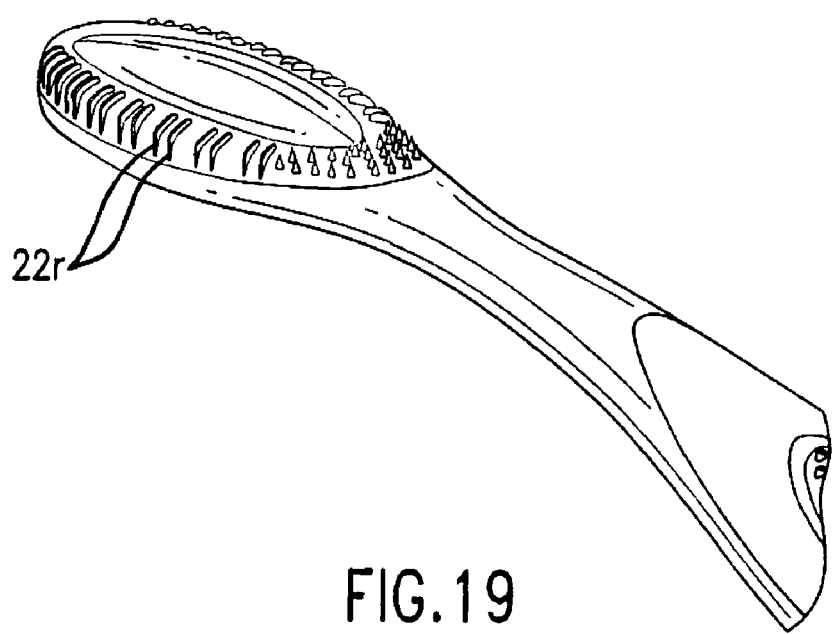
Figure 20:
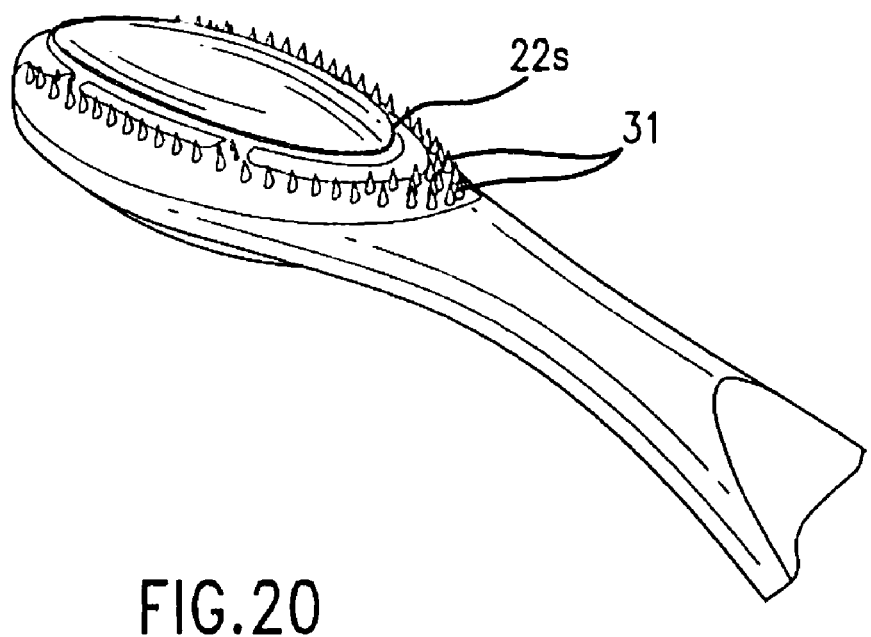
Figure 21:
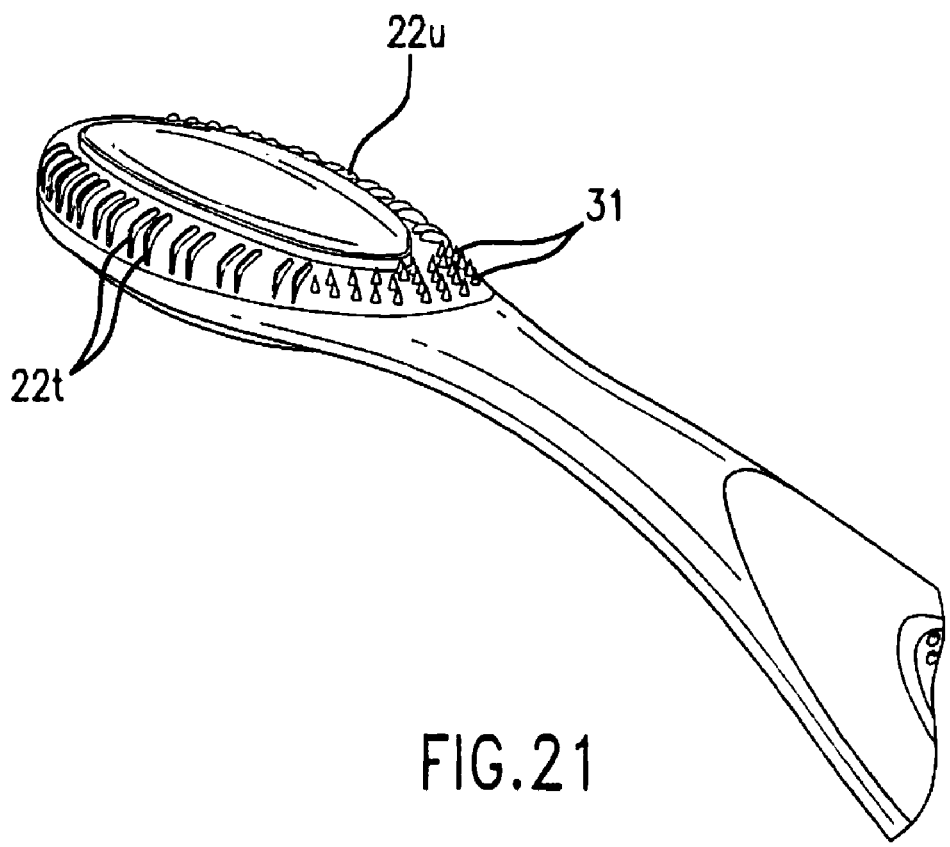
Figure 22:
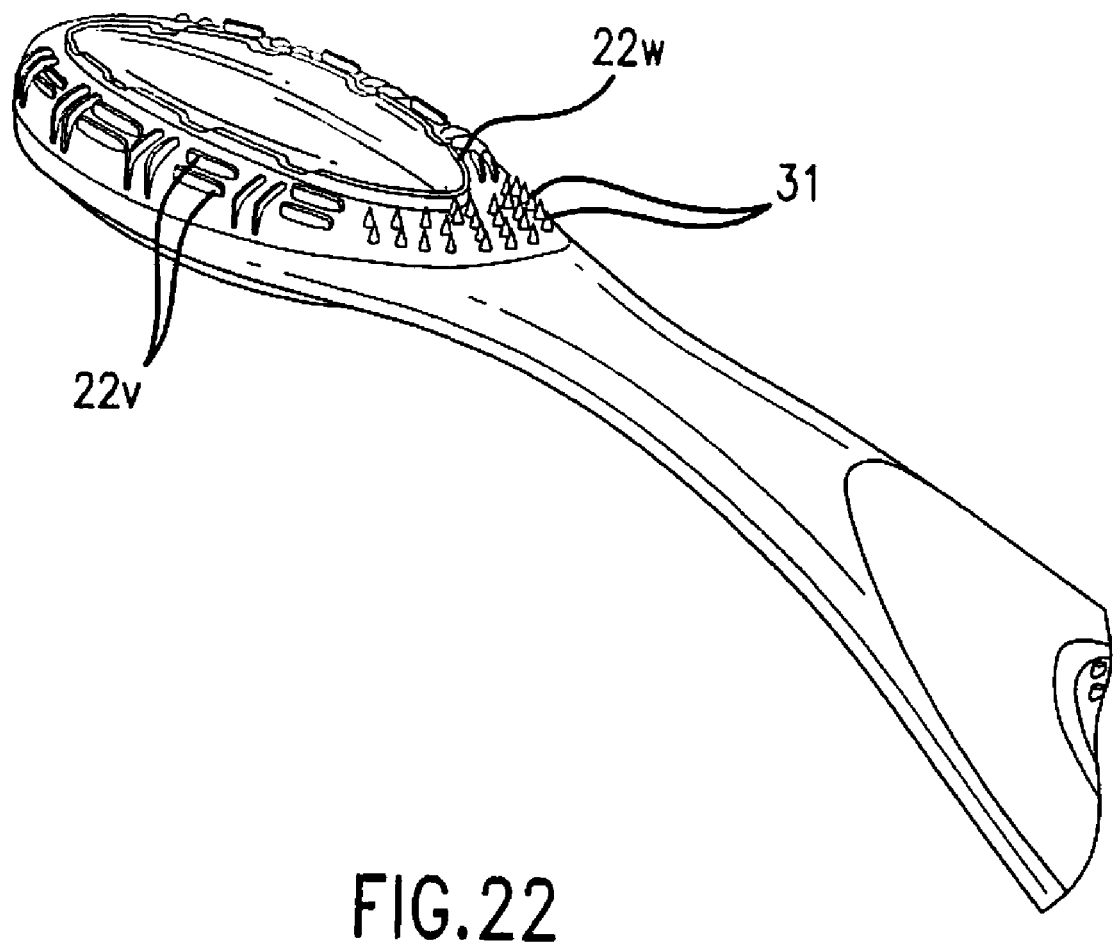

Further, other ridge constructions could be used. For example, the oral care implement could include ridges 22a that are reversed so that the concave sides face away from the handle (e.g., FIG. 4), ridges 22b, 22g, 22i, 22j, 22s with different curved shapes (e.g., FIGS. 5, 10-12, and 20), ridges 22c, 22d, 22k and 22r that are linear (e.g., FIGS. 6, 7, 13 and 19), ridges 22e, 22l, 22m, 22n and 22o that include a mixture of curved and linear ridges (e.g., FIGS. 8 and 14-17), or one continuous ridge member 22f, 22g forming successive ridges 22f', 22g', (e.g., FIGS. 9 and 10). The ridges could be non-concentric or curved at all the same radius of curvature. While the ridges preferably extend substantially across the entire side 17 of head 12, they could extend only part way across the head. For example, ridges 22p, 22r, 22t, 22v could be provided only along the sides of surface 17a (FIGS. 18-19 and 21-22). Ridges along the sides of head 12 could also be used with central ridges; i.e., side ridges 22p, 22t, 22v could be used with a central ridge(s) such as an oval or partially oval ridge 22q, 22u, 22w (FIGS. 18, 21 and 22), any of the ridge patterns illustrated in FIGS. 1a-c and 4-17, or another ridge pattern. Any of the ridges could also be used with various projections. e.g., conical projections 31 (see, e.g., FIGS. 16 and 18-22). Regardless of whether the ridge 22 each form a continuous segment across the head (e.g., FIG. 1a) or is defined by aligned ridge sections 22h separated by gaps 23 (e.g., FIG. 1b), they are in this application each considered a ridge. Also, regardless of whether successive ridges 22 are separated (e.g., FIG. 1a) or interconnected to define a single ridge member 22f (e.g., FIG. 9), the successive sections extending laterally across the hand are each considered to be a ridge. Concepts of this invention can be used in connection with ridges having virtually any shape or orientation along surface 17a.

Figures 1A, 1B:
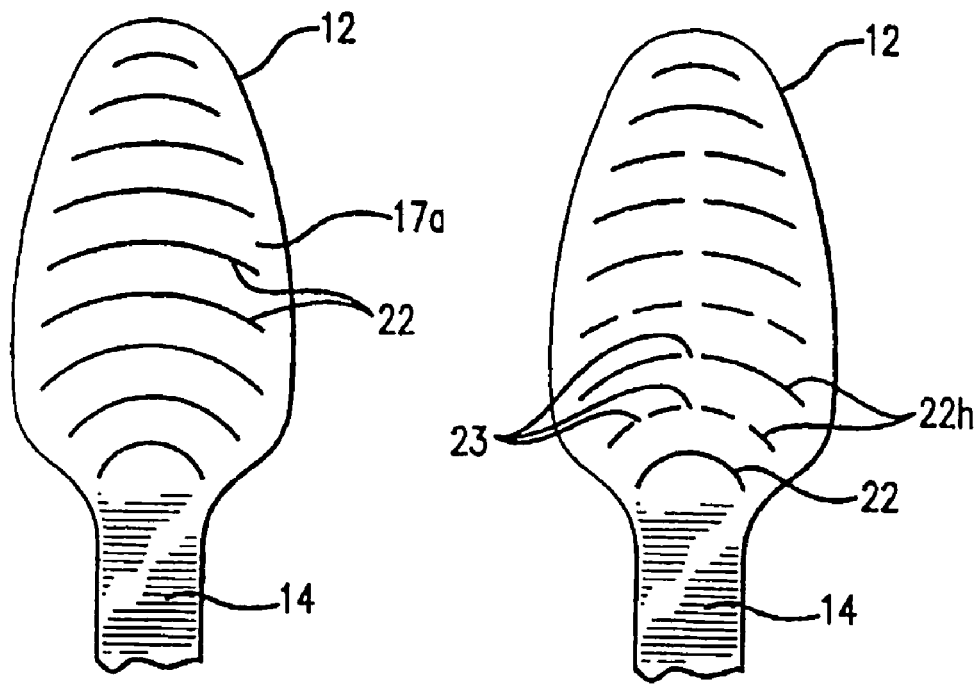
FIG. 1a is a top plan view of the head of FIG. 1.
FIGS. 1b and 1c are top plan views of the head illustrating alternative concave-shaped ridges.
Figure 1C:
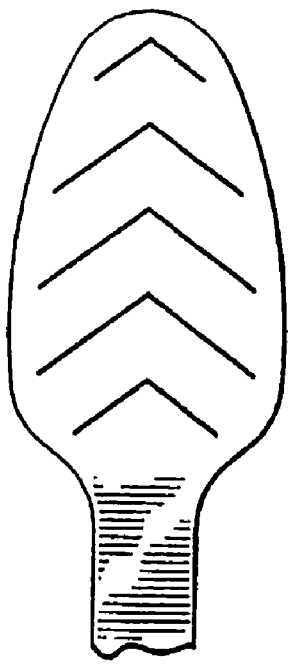

As shown in FIGS. 1 and 2, head 12, handle 14 and ridges 22 can be molded together as a one-piece member of the same material, for example, polypropylene. Nonetheless, other arrangements are possible. For example, head 12 could be detachable from handle 14. Further, ridges 22 could be separately molded, glued or otherwise attached to side 17 of head 12. The ridges as well as the head and the handle could each be made from a material different from the other parts. Soft materials, such as TPE or the like, can be fixed to head 12 to form the ridges (see, e.g., FIGS. 18-22). The ridges could be made of virtually any known material used to make oral care implements.

As various changes could be made in the above methods, compositions and structures without departing from the scope of the invention, it is intended that all matter contained in this application, including all mechanisms and/or modes of interaction described above, shall be interpreted as illustrative only and not limiting in any way the scope of the appended claims.

The invention claimed is:

1. An oral care implement comprising a handle and a head, said head including a front end remote from the handle, a rear end proximate the handle, a longitudinal axis extending generally coextensive with the handle, a first surface, a second surface that is opposite the first surface, a plurality of spaced apart elongate ridges protruding outward from the first surface, wherein at least two ridges are linear and at least two ridges are non-parallel to each other, a continuous ridge having a generally oval configuration located at the rear end of the head, wherein the at least two linear ridges are located at the front end of the head and the at least two non-parallel ridges are located between the two linear ridges and the continuous ridge, and a plurality of tooth cleaning elements protruding outward from the second surface.

2. An oral care implement in accordance with claim 1 wherein the head, handle, and the plurality of ridges are formed as a one-piece member.

3. An oral care implement comprising:
   a handle and
   a head, the head including
      a first surface,
      a second surface that is opposite the first surface,
      a plurality of elongate ridges protruding outward from the first surface, at least one of the ridges having
         a distal end remote from the first surface that defines a contact region adapted to contact and cleanse soft tissue within the mouth, the contact region having a width extending transverse to the ridge, and
         a height extending from the first surface to the distal end, the width being at least as large as the height,
      the plurality of ridges further including at least two curved ridges, with each said curved ridge has a progressively broader curvature the farther such ridge is positioned from the handle wherein the plurality of ridges includes at least one linear and non-linear ridge, and
   a plurality of tooth cleaning elements protruding outward from the second surface.

* * * * *